United States Patent [19]

Gordon et al.

[11] Patent Number: 4,474,778

[45] Date of Patent: Oct. 2, 1984

[54] LACTAM CONTAINING COMPOUNDS, THEIR PHARMACEUTICAL COMPOSITIONS AND METHOD OF USE

[75] Inventors: Eric M. Gordon, Pennington; Donald S. Karanewsky, East Windsor, both of N.J.

[73] Assignee: E. R. Squibb & Sons, Inc., Princeton, N.J.

[21] Appl. No.: 549,931

[22] Filed: Nov. 9, 1983

[51] Int. Cl.³ .................... A61K 31/55; C07D 403/12; C07D 403/14
[52] U.S. Cl. .................................. 424/244; 424/263; 424/267; 424/274; 424/273 R; 424/278; 424/275; 546/243; 546/193; 546/194; 546/201; 546/212; 546/213; 546/214; 546/216; 546/209; 260/239.3 R
[58] Field of Search ............... 546/243, 193, 194, 201, 546/212, 213, 214, 216, 209; 260/239.3 R; 424/244, 267, 263, 275, 278, 274, 273 R

[56] References Cited

U.S. PATENT DOCUMENTS 4,409,146 10/1983 Thorsett et al. ............. 260/239.3 R

FOREIGN PATENT DOCUMENTS 46289 2/1982 European Pat. Off. ..... 260/239.3 R
46291 2/1982 European Pat. Off. ..... 260/239.3 R
46292 2/1982 European Pat. Off. ..... 260/239.3 R

OTHER PUBLICATIONS

Meyer et al., "Angiotensin Converting Enzyme Inhibitors . . . ", J. Med. Chem., 1982, vol. 25, pp. 996–999.

*Primary Examiner*—Robert T. Bond
*Attorney, Agent, or Firm*—Lawrence S. Levinson; Stephen B. Davis

[57] ABSTRACT

Compounds of the formula

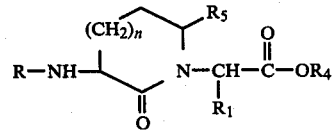

are disclosed wherein R is

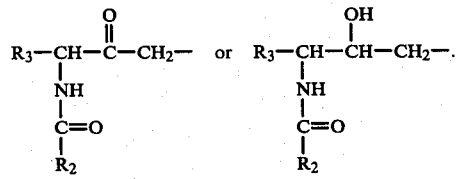

The compounds possess hypotensive activity.

22 Claims, No Drawings

LACTAM CONTAINING COMPOUNDS, THEIR PHARMACEUTICAL COMPOSITIONS AND METHOD OF USE

BACKGROUND OF THE INVENTION

Harris et al. in European patent application No. 46,289 disclose that various substituted enantholactam derivatives possess angiotensin converting enzyme inhibition activity.

Harris et al. in European patent application No. 46,291 disclose that various substituted caprolactam derivatives possess angiotensin converting enzyme inhibition activity.

Harris et al. in European patent application No. 46,292 dislcose that various substituted caprylolactam derivatives possess angiotensin converting enzyme inhibition activity.

Meyer et al., "Angiotensin Converting Enzyme Inhibitors:modifications Of A Tripeptide Analogue", J. Med. Chem., 1982, 25, 996–999, disclose the synthesis and activity of compounds of the formula

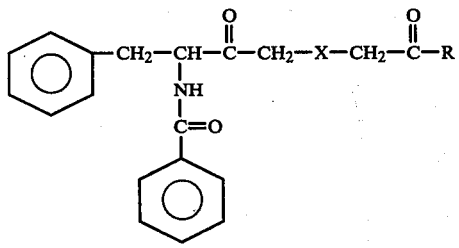

wherein X can be NH and R and be L-proline.

RELATED APPLICATIONS

Natarajan et al. in United States patent application Ser. No. 500,581 filed June 2, 1983 disclose antihypertensive compounds of the formula wherein X is various amino or imino acids or esters.

Gordon et al in United States patent application Ser. No. 515,729 filed July 21, 1983 disclose antihypertensive compounds of the formula wherein X is various amino or imino acids or esters.

Karanewsky in U.S. Ser. No. 479,429 filed Mar. 28, 1983 disclose antihypertensive lactam compounds of the formula

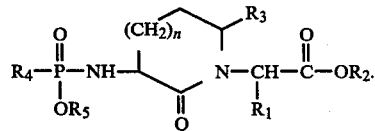

SUMMARY OF THE INVENTION

This invention is directed to the lactam compounds of formula I and salts thereof

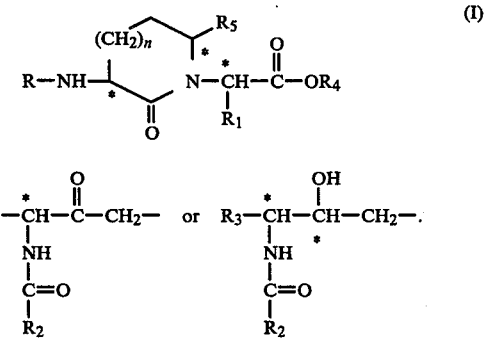

n is an integer from 1 to 4.

$R_1$ is hydrogen, lower alkyl, $-(CH_2)_r-NH_2$, $-(CH_2)_r-OH$, or halo substituted lower alkyl.

$R_5$ is hydrogen, lower alkyl, $-(CH_2)_m$-cycloalkyl,

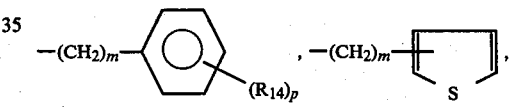

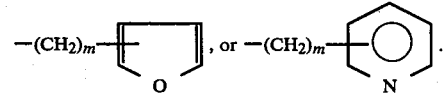

$R_2$ is

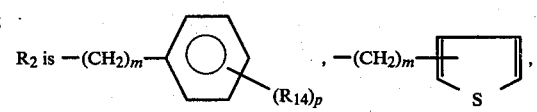

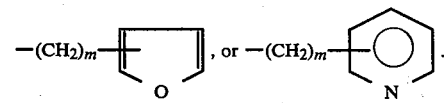

$R_3$ is hydrogen, lower alkyl,

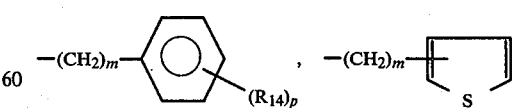

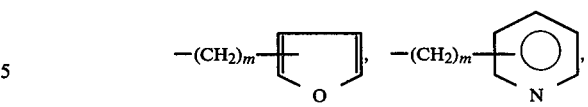

halo substituted lower alkyl, $-(CH_2)_m$-cycloalkyl,

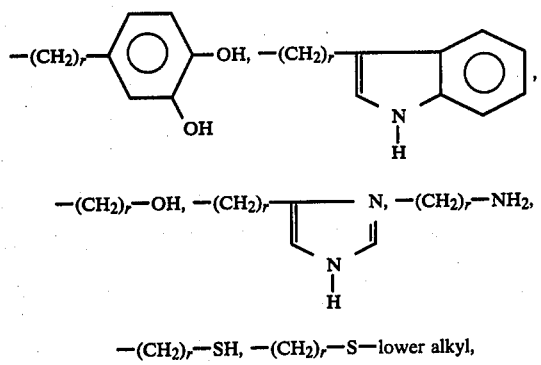

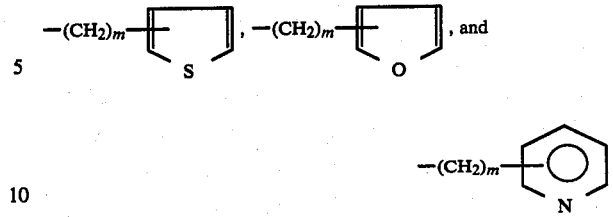

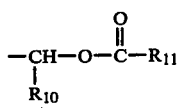

represent that the alkylene bridge is attached to an available carbon atom.

m is zero or an integer from 1 to 4.
$R_{14}$ is hydrogen, lower alkyl of 1 to 4 carbons, lower alkoxy of 1 to 4 carbons, lower alkylthio of 1 to 4 carbons, halo, trifluoromethyl, or hydroxy.
p is an integer from 1 to 3 provided that p is more than one only if $R_{14}$ is hydrogen, methyl, methoxy, chloro, or fluoro.
r is an integer from 1 to 4.
$R_4$ is hydrogen, lower alkyl, benzyl, benzhydryl, salt forming ion, or

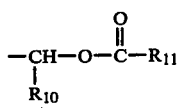

$R_{10}$ is hydrogen, lower alkyl, cycloalkyl, or phenyl.
$R_{11}$ is hydrogen, lower alkyl, lower alkoxy, cycloalkyl, phenyl, benzyl, or phenethyl.

DETAILED DESCRIPTION OF THE INVENTION

This invention in its broadest aspects relates to the lactam compounds of formula I above, to compositions containing such compounds and to the method of using such compounds as antihypertensive agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

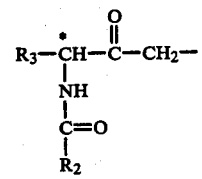

The compounds of formula I wherein R is

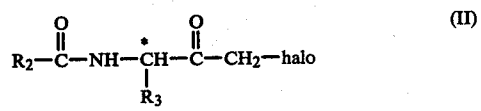

are prepared by coupling a ketone of the formula

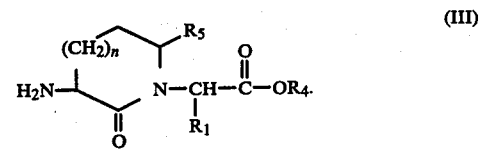

wherein halo is Cl or Br with the lactam ester of the formula $$R_2-\overset{O}{\overset{\|}{C}}-NH-\overset{*}{\underset{R_3}{C}}H-\overset{O}{\overset{\|}{C}}-CH_2-halo \qquad (II)$$

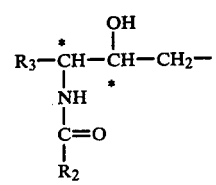

Preferably, the lactam ester of formula III is in its trifluoroacetic acid salt form and $R_4$ is lower alkyl, benzyl, or benzhydryl.

The corresponding products of formula I wherein $R_4$ is lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_4$ is hydrogen.

The compounds of formula I wherein R is

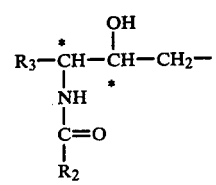

are prepared by treating a compound of formula I

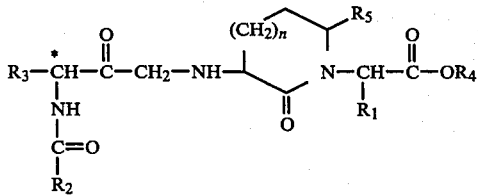

with a conventional reducing agent such as sodium borohydride, sodium cyanoborohydride, diisobutyl aluminum hydride, lithium tri t-butoxy aluminum hydride, etc.

Preferably, the above reduction is performed on an ester of formula I, i.e., $R_4$ is lower alkyl, benzyl or benzhydryl. The resulting ester product can then be deprotected, for example by hydrogenation, as described above to yield the corresponding product wherein $R_4$ is hydrogen.

The ester products of formula I wherein $R_4$ is

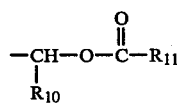

may be obtained by employing the lactam of formula III in the above reaction with the ester group already in place.

The ester products of formula I wherein $R_4$ is

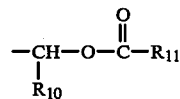

can also be obtained by treating the product of formula I wherein $R_4$ is hydrogen with a molar equivalent of the compound of the formula

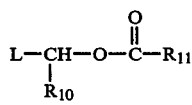  (IV)

wherein L is a leaving group such as chlorine, bromine, tolylsulfonyloxy, etc.

The ketone intermediate of formula II can be prepared by treating a ketone of the formula

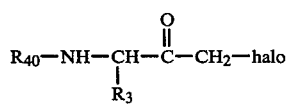  (V)

wherein $R_{40}$ is a protecting group such as benzyloxycarbonyl with hydrogen bromide and acetic acid followed by reaction with the acid halide of the formula

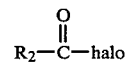  (VI)

in the presence of base such as sodium bicarbonate.

The lactam esters of formula III are prepared according to ring closure processes described in the literature and the Harris et al. applications described above.

In the above reactions if any or all of $R_1$, $R_2$, $R_3$, and $R_5$ are —$(CH_2)_r$—$NH_2$, —$(CH_2)_r$—OH,

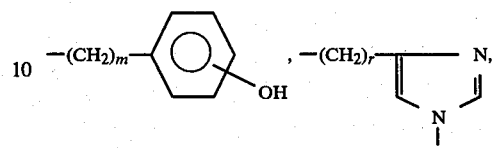

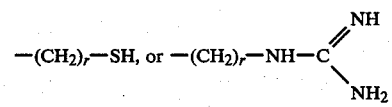

then the hydroxyl, amino, imidazolyl, mercaptan or guanidinyl function should be protected during the reaction. Suitable protecting groups include benzyloxycarbonyl, t-butoxycarbonyl benzyl, benzhydryl, trityl, etc., and nitro in the case of guanidinyl. The protecting group is removed by hydrogenation, treatment with acid, or other known methods following completion of the reaction.

Preferred compounds of this invention are those of formula I wherein:

$R_4$ is hydrogen, alkali metal salt ion, or

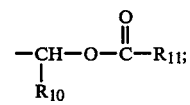

especially hydrogen.

$R_{10}$ is hydrogen, straight or branched chain lower alkyl of 1 to 4 carbons, or cyclohexyl.

$R_{11}$ is straight or branched chain lower alkyl of 1 to 4 carbons, cyclohexyl or phenyl.

$R_1$ is hydrogen, straight or branched chain lower alkyl of 1 to 4 carbons, or —$(CH_2)_4$—$NH_2$; especially hydrogen.

$R_5$ is hydrogen, lower alkyl of 1 to 4 carbons, or

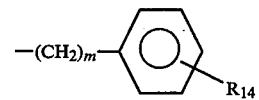

wherein m is zero, one or two and $R_{14}$ is hydrogen, methyl, methoxy, methylthio, Cl, Br, F, or hydroxy; especially hydrogen.

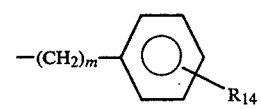

wherein m is zero, one, or two and $R_{14}$ is hydrogen, methyl, methoxy, methylthio, Cl, Br, F, or hydroxy; especially phenyl.

$R_3$ is straight or branched chain lower alkyl of 1 to 4 carbons, —$(CH_2)_r$—$NH_2$,

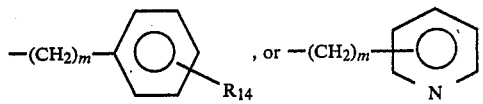

wherein m is zero, one, or two, $R_{14}$ is hydrogen, methyl, methoxy, methylthio, Cl, Br, F, or hydroxy, and r is an integer from 1 to 4; especially benzyl.

The compounds of this invention wherein $R_4$ is hydrogen form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The symbol * is used to represent various asymmetric centers which may be present in the compounds of formula I. Thus, the compounds of this invention can accordingly exist in diastereoisomeric forms or in mixtures thereof. The above described processes can utilize racemates, enantiomers or diasteromers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensin→(renin)-→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlomethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 100 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene-divinylbenzene sulfonic acid cation exchange resin. HP-20 refers to a porous crosslinked polystyrene divinylbenzene polymer resin.

EXAMPLE 1

(S)-3-[[3-(Benzoylamino)-2-oxo-4-phenylbutyl]-amino]-hexahydro-2-oxo-1H-azepine-1-acetic acid (a) $N^2$-[(1,1-Dimethylethoxy)carbonyl]-$N^6$-[(phenylmethoxy)carbonyl]-L-lysine,methyl ester $N^2$-[(1,1-Dimethylethoxy)carbonyl]-$N^6$-[(phenylmethoxy)carbonyl]-L-lysine (25 g., 65.7 mmole) is dissolved in dimethylformamide (125 ml.) then sodium bicarbonate (11.05 g., 131.4 mmole) and finally methyl iodide (20.5 ml., 330 mmole) are added. The reaction mixture is allowed to stir at room temperature under a nitrogen atmosphere overnight. It is then poured into water (400 ml.) and extracted with ethyl acetate (3×200 ml.). The combined ethyl acetate extracts are washed with saturated sodium bicarbonate (3×), water (3×), dried ($Na_2SO_4$), and concentrated to give 25.0 g. of $N^2$-[(1,1-dimethylethoxy)carbonyl]-$N^6$-[(phenylmethoxy)carbonyl]-L-lysine, methyl ester as an oily residue.

(b) (S)-3-[[(1,1-Dimethylethoxy)carbonyl]amino]-2-oxo-hexahydro-1H-azepine

A mixture of $N^2$-[(1,1-dimethylethoxy)carbonyl]-$N^6$-[(phenylmethoxy)carbonyl]-L-lysine, methyl ester (25.0 g., 63.3 mmole), 10% palladium on carbon catalyst (2.5 g.), in ethanol (95%, 250 ml.) is hydrogenated at atmospheric pressure overnight. The catalyst is removed by filtration and the filtrate is evaporated. The resulting oily residue is dissolved in xylene (150 ml.) and refluxed for 24 hours. The xylene is diluted with ethyl acetate and washed with 5% potassium bisulfate (2×150 ml.), saturated sodium bicarbonate (2×150 ml.), water (2×150 ml.), dried ($Na_2SO_4$) and concentrated to give 7.4 g. of (S)-3-[[(1,1-dimethylethoxy)carbonyl]amino]-2-oxo-hexahydro-1H-azepine as a solid residue.

(c) (S)-3-[[(1,1-Dimethylethoxy)carbonyl]amino]-2-oxo-hexahydro-1H-azepine-1-acetic acid, phenylmethyl ester A mixture of (S)-3-[[(1,1-dimethylethoxy)carbonyl]amino]-2-oxo-hexahydro-1H-azepine (7.4 g., 32.4 mmole) and potassium tert-butoxide (4.72 g., 42.1 mmole) in tetrahydrofuran (distilled, 50 ml.) is stirred at room temperature for 15 minutes until a clear solution is obtained. Benzyl bromoacetate (8.75 ml., 55 mmole) is added via dropping funnel over a 10 minute period. After 4 hours, the reaction mixture is diluted with ethyl acetate (300 ml.), washed successively with saturated sodium bicarbonate, 10% potassium bisulfate, and water, dried ($Na_2SO_4$), and concentrated into an oily residue (15 g.). Flash chromatography (400 g. Merck silica gel, 15% ethyl acetate/methylene chloride) affords 8.2 g. of pure (S)-3-[[(1,1-dimethylethoxy)carbonyl]amino]-2-oxo-hexahydro-1H -azepine-1-acetic acid, phenylmethyl ester as a pale yellow oil.

(d) (S)-3-Amino-2-oxo-hexahydro-1H-azepine-1-acetic acid, phenylmethyl ester, trifluoroacetic acid salt (S)-3-[[(1,1-Dimethylethoxy)carbonyl]amino]-2-oxo-hexahydro-1H-azepine-1-acetic acid, phenylmethyl ester (3.01 g., 8 mmole) is added to trifluoroacetic acid (30 ml.) containing anisole (0.3 ml.). After stirring at room temperature for one hour, the volatiles are removed in vacuo and the residue is chased with toluene (2×). The oily residue is triturated with ether (5×) to obtain a colorless oil. Drying in high vacuum gives 2.24 g. of (S)-3-amino-2-oxo-hexahydro-1H-azepine-1-acetic acid, phenylmethyl ester, trifluoroacetic acid salt as a dried foam.

(e) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45 N, 348 ml.) and kept at room temperature for 1.5 hours. The reaction mixture is then concentrated in vacuo and precipitated with ether to contain 36.6 g. of (S)-3-amino-1-chloro-4-phenyl-2-butanone, hydrogen bromide; m.p. (175°) 177°-179°.

(f) (S)-N-[3-Chloro-2-oxo-1-(phenylmethyl)propyl]benzamide (S)-3-Amino-1-chloro-4-phenyl-2-butanone, hydrogen bromide (36.3 g., 130.3 mmole) is suspended in 520 ml. of dry tetrahydrofuran and 18.2 ml. of triethylamine (130.3 mmole) with stirrin for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2-oxo-1-(phenylmethyl)propyl]-benzamide; m.p. (160°) 170°-172° (dec.); $[\alpha]_D^{23} = -129$ (c 1.7, dimethylformamide).

(g) (S)-3-[[(3-(Benzoylamino)-2-oxo-4-phenylbutyl]amino]-hexahydro-2-oxo-1H-azepine-1-acetic acid A reaction mixture of (S)-3-amino-2-oxohexahydro-1H-azepine-1-acetic acid, phenylmethyl ester, trifluoroacetic acid salt (1.79 g., 4.6 mmole), (S)-N-[3-chloro-2-oxo-1-(phenylmethyl)propyl]benzamide (1.38 g., 4.6 mmole), excess sodium bicarbonate, sodium iodide (0.68 g., 4.6 mmole) and diisopropylethylamine (0.59 g., 0.79 ml., 4.6 mmole) in dimethylformamide (12 ml.) is stirred at room temperature overnight under a nitrogen atmosphere. The reaction mixture is concentrated and the residue is partitioned between water/ethyl acetate. The layers separate and the aqueous layer is extracted once more with ethyl acetate. The combined organic extracts are washed with saturated sodium bicarbonate, 10% potassium bisulfate, water, dried ($Na_2SO_4$), and concentrated into an oily residue (1.4 g.). Flash chromatography (150 g. silica gel, 25% ethyl acetate/methylene chloride) affords (S)-3-[[3-(benzoylamino)-2-oxo-4-phenylbutyl]amino]hexahydro-2-oxo-1H-azepine-1-acetic acid, phenylmethyl ester as two very similar products. Product A (0.53 g., yellow oil) TLC (silica gel, 5% methanol/ethyl acetate) $R_f=0.56$ and product B (0.01 g., yellow oil) TLC (silica gel, 5% methanol/ethyl acetate) $R_f=0.54$.

Both products are hydrogenated separately overnight in acidic (1N hydrochloric acid) ethanol (95%) containing 10% palladium on carbon catalyst. After removal of the catalyst, the filtrates are concentrated and the residue is triturated with ether. The products are obtained as a pale yellow oil which becomes dry upon high vacuum drying and which have the same $R_f$ values. The products are combined (0.28 g.) and purified on an HP-20 column (methanol/water) affording 20 mg. of (S)-3-[[3-(benzoylamino)-2-oxo-4-phenylbutyl]amino]-hexahydro-2-oxo-1H-azepine-1-acetic acid as a white solid material; m.p. 88°-91°; TLC (silica gel, n-butanol/acetic acid/water, 4/1/1) $R_f=0.57$.

Anal. calc'd. for $C_{25}H_{29}N_3O_5 \cdot CH_3OH$: C, 64.57; H, 6.87; N, 8.69. Found: C, 64.55; H, 6.26; N, 8.22.

EXAMPLES 2–37

Following the procedure of Example 1 but employing the lactam ester shown in Col. I and the ketone shown in Col. II, one obtains the ester product shown in Col. III.

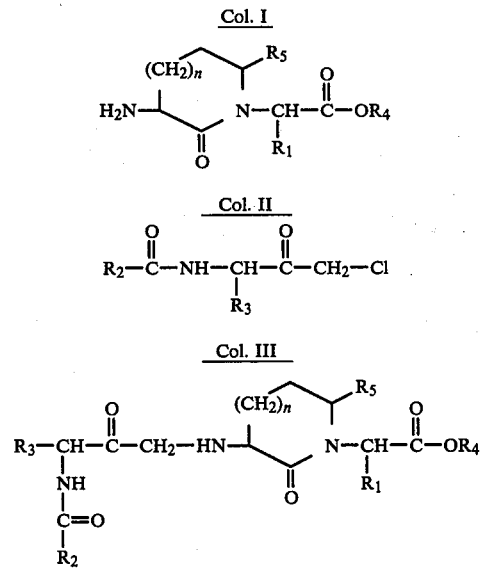

| Example | n | $R_1$ | $R_5$ | $R_4$ | $R_3$ | $R_2$ |
|---|---|---|---|---|---|---|
| 2 | 1 | —H | —H | —CH$_2$—Ph | —CH$_2$—Ph | —Ph |
| 3 | 3 | —H | —H | —CH$_2$—Ph | —CH$_2$—Ph | —Ph |
| 4 | 4 | —H | —H | —CH$_2$—Ph | —CH$_2$—Ph | —Ph |
| 5 | 2 | —CH$_3$ | —H | —CH$_2$—Ph | —(CH$_2$)$_2$—Ph | —Ph |
| 6 | 1 | —(CH$_2$)$_4$—NH—C(=O)—O—CH$_2$—Ph | —H | —CH$_2$—Ph | —(CH$_2$)$_4$—C$_6$H$_{11}$ | —Ph |
| 7 | 2 | —CH$_2$—O—CH$_2$—Ph | —H | —CH$_2$—Ph | —(CH$_2$)$_2$—C$_6$H$_4$—CH$_3$ | —Ph |
| 8 | 3 | —CH$_3$ | —CH$_3$ | —CH$_2$—Ph | —Ph | —CH$_2$—Ph |
| 9 | 4 | —CH$_3$ | —C$_2$H$_5$ | —CH$_2$—Ph | —CH$_2$-thienyl | —Ph |
| 10 | 1 | —H | —CH$_3$ | —CH$_2$—Ph | —(CH$_2$)$_2$-furyl | —Ph |
| 11 | 2 | —H | —Ph | —CH$_2$—Ph | —CH$_2$—Ph | —Ph |
| 12 | 3 | —H | —CH$_2$—Ph | —CH$_2$—Ph | —(CH$_2$)$_4$-pyridyl | —Ph |

-continued

| Example | n | $R_1$ | $R_2$ | $R_3$ | $R_4$ | $R_5$ |
|---|---|---|---|---|---|---|
| 13 | 4 | —H | —C₆H₅ | —CH₂-(3-pyridyl) | —CH₂—C₆H₅ | —CH₂-(2-thienyl) |
| 14 | 1 | —H | —C₆H₅ | —C₃H₇ | —CH₂—C₆H₅ | —CH₂-(2-furyl) |
| 15 | 2 | —H | —C₆H₅ | —CH₂—C₆H₅ | —CH₂—C₆H₅ | —CH₂-(3-pyridyl) |
| 16 | 3 | —H | —C₆H₅ | —CH₂—C₆H₄Cl | —CH₂—C₆H₅ | cyclohexyl |
| 17 | 4 | —H | —(CH₂)—(2-thienyl) | —CH₂—C₆H₅ | —CH(C₆H₅)₂ | —H |
| 18 | 1 | —H | —CH₂-(2-furyl) | —CH₂—C₆H₅ | —CH₂—C₆H₅ | —H |
| 19 | 2 | —CH₃ | -(4-pyridyl) | —(CH₂)₄—C₆H₅ | —CH₂—C₆H₅ | —H |
| 20 | 3 | —H | —C₆H₅ | —H | —CH₂—C₆H₅ | cyclohexyl |
| 21 | 4 | —H | —C₆H₅ | —CH₂-cyclohexyl | —CH₂—C₆H₅ | —H |
| 22 | 1 | —H | -(4-methylcyclohexyl) | —CH₂CCl₃ | —CH₂—C₆H₅ | —H |

-continued

| Example | n | $R_1$ | $R_5$ | $R_4$ | $R_3$ | $R_2$ |
|---|---|---|---|---|---|---|
| 23 | 2 | —H | —C$_6$H$_5$ (phenyl) | —CH$_2$—C$_6$H$_5$ | —CH$_2$—C$_6$H$_4$—OCH$_2$—C$_6$H$_5$ | —C$_6$H$_5$ |
| 24 | 3 | —H | —H | —CH$_2$—C$_6$H$_5$ | —CH$_2$—C$_6$H$_3$(OCH$_2$—C$_6$H$_5$)$_2$ | —C$_6$H$_5$ |
| 25 | 4 | —CH$_3$ | —H | —CH$_2$—C$_6$H$_5$ | —CH$_2$-(indol-3-yl) | —C$_6$H$_5$ |
| 26 | 1 | —H | —H | —CH$_2$—C$_6$H$_5$ | —CH$_2$—O—CH$_2$—C$_6$H$_5$ | —C$_6$H$_5$ |
| 27 | 2 | —H | —H | —CH$_2$—C$_6$H$_5$ | —CH$_2$-(N-benzyloxycarbonyl-imidazolyl) | —C$_6$H$_5$ |
| 28 | 3 | —H | —H | —CH$_2$—C$_6$H$_5$ | —(CH$_2$)$_4$—NH—C(O)—O—CH$_2$—C$_6$H$_5$ | —CH$_2$—C$_6$H$_5$ |
| 29 | 4 | —H | —H | —CH$_2$—C$_6$H$_5$ | —CH$_2$—S—CH$_2$—C$_6$H$_5$ | —C$_6$H$_5$ |
| 30 | 1 | —H | —H | —CH$_2$—C$_6$H$_5$ | —CH$_2$—S—(CH$_3$)$_2$ | —C$_6$H$_5$ |
| 31 | 2 | —H | —H | —CH$_2$—C$_6$H$_5$ | —CH$_2$—NH—C(=NH)—NH$_2$·NO$_2$ | —C$_6$H$_5$ |

-continued

| Example | n | $R_1$ | $R_4$ | $R_3$ | $R_2$ | $R_5$ |
|---|---|---|---|---|---|---|
| 32 | 3 | —H | —CH$_2$—C$_6$H$_5$ | —CH$_2$—C(=O)—NH$_2$ | —C$_6$H$_5$ | —H |
| 33 | 4 | —H | —CH$_2$—O—C(=O)—C(CH$_3$)$_3$ | —CH$_2$—C$_6$H$_5$ | —C$_6$H$_5$ | —H |
| 34 | 1 | —H | —CH(—C$_6$H$_{11}$)—O—C(=O)—C$_2$H$_5$ | —CH$_2$—C$_6$H$_5$ | —C$_6$H$_5$ | —H |
| 35 | 2 | —H | —CH(—CH(CH$_3$)$_2$)—O—C(=O)—C$_2$H$_5$ | —CH$_2$—C$_6$H$_5$ | —C$_6$H$_5$ | —H |
| 36 | 3 | —H | —CH$_2$—O—C(=O)—C$_6$H$_5$ | —CH$_2$—C$_6$H$_5$ | —C$_6$H$_5$ | —H |
| 37 | 4 | —H | —CH$_2$—O—C(=O)—C$_6$H$_{11}$ | —CH$_2$—C$_6$H$_5$ | —C$_6$H$_5$ | —C$_6$H$_5$ |

The ester products of Examples 2 to 32 can be hydrogenated according to the procedure of Example 1 (g) to yield the corresponding acid products, i.e., $R_4$ is hydrogen. The $R_4$ ester groups shown in Examples 33 to 37 would not be removed.

The $R_1$ protecting groups shown in Examples 6 and 7 and the $R_3$ protecting groups shown in Examples 23, 24, 26, 27, 28, 29 and 31 would be removed following completion of the coupling reaction.

EXAMPLE 38

(S)-3-[[3-(Benzoylamino)-2-hydroxy-4-phenylbutyl]amino]-hexahydro-2-oxo-1H-azepine-1-acetic acid (a) (S)-3-[[3-(Benzoylamino)-2-hydroxy-4-phenylbutyl]amino]-hexahydro-2-oxo-1H-azepine-1-acetic acid, phenylmethyl ester To a solution of (S)-3-[[3-(benzoylamino)-2-oxo-4-phenylbutyl]amino]-hexahydro-2-oxo-1H-azepine-1-acetic acid, phenylmethyl ester (2.5 mmole) in tetrahydrofuran (25 ml.) and water (2.5 ml.) is added sodium borohydride (10.0 mmole) portionwise over a 10 minute period. After the addition is completed, the reaction mixture is stirred for 4 hours, and slowly quenched with concentrated hydrochloric acid. The mixture is diluted with ethyl acetate (50 ml.), washed with water (2×), saturated sodium bicarbonate (2×), and saturated sodium chloride (2×), dried ($Na_2SO_4$), and concentrated under reduced pressure to give (S)-3-[[3-(benzoylamino)-2-hydroxy-4-phenylbutyl]amino]hexahydro-2-oxo-1H-azepine-1-acetic acid, phenylmethyl ester.

(b) (S)-3-[[3-(Benzoylamino)-2-hydroxy-4-phenylbutyl]amino]-hexahydro-2-oxo-1H-azepine-1-acetic acid A solution of the phenylmethyl ester product from part (a) (2.0 mmole) in 95% ethanol (50 ml.) containing 10% palladium on carbon catalyst (0.2 g.) is hydrogenated under atmospheric pressure overnight. The catalyst is filtered, washed with 95% ethanol and the filtrate concentrated under reduced pressure into an oily residue which is then treated for 5 minutes with 1.4N hydrochloric acid/acetic acid (10 ml.). The reaction mixture is concentrated under reduced pressure to yield a solid residue. The crude product is purified on an HP-20 column (5% methanol/0.01N hydrochloric acid→90% methanol/0.01N hydrochloric acid) to give (S)-3-[[3-(benzoylamino)-2-hydroxy-4-phenylbutyl]amino]-hexahydro-2-oxo-1H-azepine-1-acetic acid.

In a similar manner, the keto ester shown in Col. III of Examples 2 to 37 can be treated with sodium borohydride to yield the corresponding alcohol ester products. In the case of Examples 2 to 32, hydrogenation then yields the alcohol acetic acid products.

EXAMPLE 39

(S)-3-[[3-(Benzoylamino)-2-oxo-4-phenylbutyl]amino]-hexahydro-2-oxo-1H-azepine-1-acetic acid, sodium salt (S)-3-[[3-(Benzoylamino)-2-oxo-4-phenylbutyl]amino]-hexahydro-2-oxo-1H-azepine-1-acetic acid (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm.×60 cm.) of Sephadex chromatography gel G-10 and eluted with water. Fractions containing the desired product are pooled and lyophilized to give (S)-3-[[3-(benzoylamino)-2-oxo-4-phenylbutyl]amino]-hexahydro-2-oxo-1H-azepine-1-acetic acid, sodium salt.

EXAMPLE 40

1000 tablets each containing the following ingredients:

| | |
|---|---|
| (S)—3-[[3-(Benzoylamino)-2-oxo-4-phenylbutyl]amino]-hexahydro-2-oxo-1H—azepine-1-acetic acid, sodium salt | 100 mg. |
| Corn starch | 50 mg. |
| Gelatin | 7.5 mg. |
| Avicel (microcrystalline cellulose) | 25 mg. |
| Magnesium stearate | 2.5 mg. | are prepared from sufficient bulk quantities by mixing the (S)-3-[[3-(benzoylamino)-2-oxo-4-phenylbutyl]amino]-hexahydro-2-oxo-1H-azepine-1-acetic acid, sodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 38 can be prepared.

A similar procedure can be employed to form tablets containing 50 mg. of active ingredient.

EXAMPLE 41

Two piece #1 gelatin capsules each containing 50 mg. of (S)-3-[[3-(benzoylamino)-2-hydroxy-4-phenylbutyl]amino]-hexahydro-2-oxo-1H-azepine-1-acetic acid, sodium salt are filled with a mixture of the following ingredients:

| | |
|---|---|
| (S)—3-[[3-(Benzoylamino)-2-hydroxy-4-phenylbutyl]amino]-hexahydro-2-oxo-1H—azepine-1-acetic acid, sodium salt | 50 mg. |
| Magnesium stearate | 7 mg. |
| Lactose | 193 mg. |
| | 250 mg. |

In a similar manner capsules containing 50 mg. of the product of any of Examples 1 to 39 can be prepared.

EXAMPLE 42

An injectable solution is prepared as follows:

| | |
|---|---|
| (S)—3-[[3-(Benzoylamino)-2-oxo-4-phenylbutyl]amino]-hexahydro-2-oxo-1H—azepine-1-acetic acid, sodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1 to 38.

EXAMPLE 43

1000 tablets each containing the following ingredients:

| | |
|---|---|
| (S)—3-[[3-(Benzoylamino)-2-oxo-4-phenylbutyl]amino]-hexahydro-2-oxo-1H—azepine-1-acetic acid, sodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the (S)-3-[[3-(benzoylamino)-2-oxo-4-phenylbutyl]amino]-hexahydro-2-oxo-1H-azepine-1-acetic acid, sodium, Avicel and a portion of the stearic acid. The slugs are ground and passed through a #12 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 38.

What is claimed is:

1. A compound of the formula $$R-NH-\overset{\overset{(CH_2)_n}{|}}{\underset{\underset{O}{\|}}{C}}-N-\overset{R_5}{\underset{R_1}{\overset{|}{C}H}}-\overset{O}{\overset{\|}{C}}-OR_4$$

or a pharmaceutically acceptable salt therein wherein:

R is $R_3-\underset{\underset{\underset{R_2}{C=O}}{\overset{|}{NH}}}{\overset{|}{C}H}-\overset{O}{\overset{\|}{C}}-CH_2-$ or $R_3-\underset{\underset{\underset{R_2}{C=O}}{\overset{|}{NH}}}{\overset{|}{C}H}-\overset{OH}{\overset{|}{C}H}-CH_2-$;

n is an integer from 1 to 4;

$R_1$ is hydrogen, lower alkyl, —(CH₂)_r—NH₂, —(CH₂)_r—OH, or halo substituted lower alkyl;

$R_5$ is hydrogen, lower alkyl, —(CH₂)_m-cycloalkyl wherein said cycloalkyl is a saturated ring of 3 to 7 carbons, —(CH₂)_m—⟨phenyl(R₁₄)_p⟩, —(CH₂)_m—⟨thienyl⟩, —(CH₂)_m—⟨furyl⟩, or —(CH₂)_m—⟨pyridyl⟩;

$R_2$ is —(CH₂)_m—⟨phenyl(R₁₄)_p⟩, —(CH₂)_m—⟨thienyl⟩,

—(CH₂)_m—⟨furyl⟩, or —(CH₂)_m—⟨pyridyl⟩;

$R_3$ is hydrogen, lower alkyl,

—(CH₂)_m—⟨phenyl(R₁₄)_p⟩, —(CH₂)_m—⟨thienyl⟩,

—(CH₂)_m—⟨furyl⟩, —(CH₂)_m—⟨pyridyl⟩, halo substituted lower alkyl, —(CH₂)_m-cycloalkyl wherein said cycloalkyl is a saturated ring of 3 to 7 carbons, —(CH₂)_r—⟨phenyl-OH⟩, —(CH₂)_r—⟨indolyl⟩, —(CH₂)_r—OH, —(CH₂)_r—⟨imidazolyl⟩, —(CH₂)_r—NH₂, —(CH₂)_r—SH, —(CH₂)_r—S—lower alkyl, —(CH₂)_r—NH—C(=NH)(NH₂) or —(CH₂)_r—C(=O)—NH₂;

m is zero or an integer from 1 to 4;

$R_{14}$ is hydrogen, lower alkyl of 1 to 4 carbons, lower alkoxy of 1 to 4 carbons, lower alkylthio of 1 to 4 carbons, halo, trifluoromethyl, or hydroxy;

p is an integer from 1 to 3 provided that p is more than one only if $R_{14}$ is hydrogen, methyl, methoxy, chloro, or fluoro;

r is an integer from 1 to 4;

$R_4$ is hydrogen, lower alkyl, benzyl, benzhydryl, an alkali metal salt ion, an alkaline earth metal salt ion, or $-\underset{\underset{R_{10}}{|}}{C}H-O-\overset{O}{\overset{\|}{C}}-R_{11};$ $R_{10}$ is hydrogen, lower alkyl, cycloalkyl of 3 to 7 carbons, or phenyl; and $R_{11}$ is hydrogen, lower alkyl, lower alkoxy, cycloalkyl of 3 to 7 carbons, phenyl, benzyl, or phenethyl.

2. A compound of claim 1 wherein:
$R_1$ is hydrogen, straight or branched chain lower alkyl of 1 to 4 carbons, or —(CH$_2$)$_4$—NH$_2$;
$R_5$ is hydrogen, straight or branched chain lower alkyl of 1 to 4 carbons, or

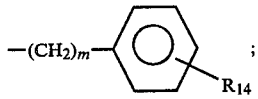

$R_2$ is —(CH$_2$)$_m$—

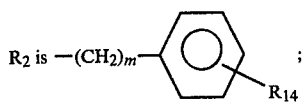

$R_3$ is straight or branched chain lower alkyl of 1 to 4 carbons, —(CH$_2$)$_r$—NH$_2$,

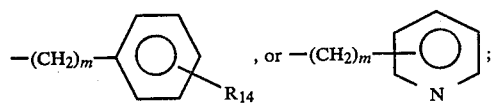

m is zero, one or two;
$R_{14}$ is hydrogen, methyl, methoxy, methylthio, Cl, Br, F, or hydroxy;
r is an integer from 1 to 4;
$R_4$ is hydrogen, alkali metal salt ion, or

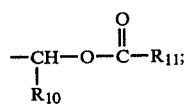

$R_{10}$ is hydrogen, straight or branched chain lower alkyl of 1 to 4 carbons, or cyclohexyl; and
$R_{11}$ is straight or branched chain lower alkyl of 1 to 4 carbons, cyclohexyl or phenyl.

3. A compound of claim 2 wherein

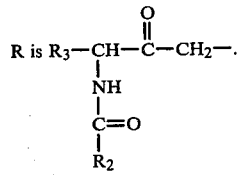

4. A compound of claim 3 wherein n is four.
5. A compound of claim 4 wherein
$R_1$ is hydrogen;
$R_5$ is hydrogen;
$R_4$ is hydrogen;
$R_2$ is phenyl; and
$R_3$ is benzyl.
6. A compound of claim 3 wherein n is three.
7. A compound of claim 6 wherein
$R_1$ is hydrogen;
$R_5$ is hydrogen;
$R_4$ is hydrogen;
$R_2$ is phenyl; and
$R_3$ is benzyl.
8. A compound of claim 3 wherein n is two.

9. A compound of claim 8 wherein
$R_1$ is hydrogen;
$R_5$ is hydrogen;
$R_4$ is hydrogen;
$R_2$ is phenyl; and
$R_3$ is benzyl.
10. A compound of claim 3 wherein n is one.
11. A compound of claim 10 wherein
$R_1$ is hydrogen;
$R_5$ is hydrogen;
$R_4$ is hydrogen;
$R_2$ is phenyl; and
$R_3$ is benzyl.
12. A compound of claim 2 wherein
R is

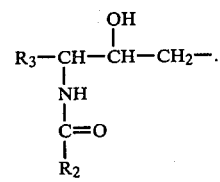

13. A compound of claim 12 wherein n is four.
14. A compound of claim 13 wherein
$R_1$ is hydrogen;
$R_5$ is hydrogen;
$R_4$ is hydrogen;
$R_2$ is phenyl; and
$R_3$ is benzyl.
15. A compound of claim 12 wherein n is three.
16. A compound of claim 15 wherein
$R_1$ is hydrogen;
$R_5$ is hydrogen;
$R_4$ is hydrogen;
$R_2$ is phenyl; and
$R_3$ is benzyl.
17. A compound of claim 12 wherein n is two.
18. A compound of claim 17 wherein
$R_1$ is hydrogen;
$R_5$ is hydrogen;
$R_4$ is hydrogen;
$R_2$ is phenyl; and
$R_3$ is benzyl.
19. A compound of claim 12 wherein n is one.
20. A compound of claim 19 wherein
$R_1$ is hydrogen;
$R_5$ is hydrogen;
$R_4$ is hydrogen;
$R_2$ is phenyl; and
$R_3$ is benzyl.
21. A pharmaceutical composition useful for treating hypertension in a mammalian species comprising a pharmaceutically acceptable carrier and an effective amount of a hypotensive compound of the formula

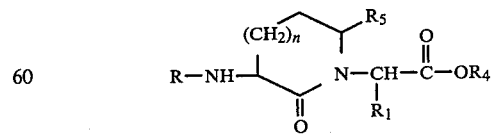

wherein n, R, $R_1$, $R_4$ and $R_5$ are as defined in claim 1.
22. The method of treating hypertension in a mammalian host which comprises administering an effective amount of the composition of claim 21.

* * * * *

UNITED STATES PATENT AND TRADEMARK OFFICE
CERTIFICATE OF CORRECTION

PATENT NO. :   4,474,778
DATED       :   October 2, 1984
INVENTOR(S) :   Eric M. Gordon et al.

It is certified that error appears in the above-identified patent and that said Letters Patent are hereby corrected as shown below:

Column 6, line 60, insert -- $R_2$ is -- .
Column 9, line 42, delete "stirfin" and insert -- stirring -- .
Column 14, Example 20, under $R_5$ the formula should read --  -- .

Column 14, Example 22, under $R_2$ the formula should read

-- 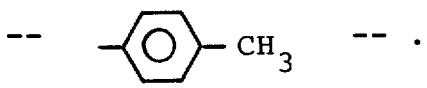 -- .

Signed and Sealed this

First Day of October 1985

[SEAL]

Attest:

DONALD J. QUIGG

Attesting Officer

Commissioner of Patents and
Trademarks—Designate